(12) United States Patent
Levine

(10) Patent No.: US 11,039,892 B2
(45) Date of Patent: Jun. 22, 2021

(54) ROBOTICALLY-ASSISTED KNEE ARTHROPLASTY SUPPORT SYSTEMS AND METHODS

(71) Applicant: Zimmer, Inc., Warsaw, IN (US)

(72) Inventor: Harlan Levine, Tenafly, NJ (US)

(73) Assignee: Zimmer, Inc., Warsaw, IN (US)

( * ) Notice: Subject to any disclaimer, the term of this patent is extended or adjusted under 35 U.S.C. 154(b) by 170 days.

(21) Appl. No.: 16/225,648

(22) Filed: Dec. 19, 2018

(65) Prior Publication Data

US 2019/0192231 A1 Jun. 27, 2019

Related U.S. Application Data

(60) Provisional application No. 62/610,064, filed on Dec. 22, 2017.

(51) Int. Cl.
*A61B 34/20* (2016.01)
*A61B 34/10* (2016.01)
*A61B 34/30* (2016.01)
*A61F 2/38* (2006.01)
*A61G 13/00* (2006.01)
(Continued)

(52) U.S. Cl.
CPC ............. *A61B 34/20* (2016.02); *A61B 34/10* (2016.02); *A61B 34/30* (2016.02); *A61F 2/38* (2013.01); *A61G 13/00* (2013.01); *A61B 17/1764* (2013.01); *A61B 2034/102* (2016.02); *A61B 2034/108* (2016.02); *A61B 2034/2048* (2016.02); *A61B 2034/2055* (2016.02); *A61B 2034/2057* (2016.02); *A61B 2034/305* (2016.02); *A61B 2090/064* (2016.02)

(58) Field of Classification Search
CPC ......... A61B 34/20; A61B 34/10; A61B 34/30; A61B 2034/102; A61B 2034/108; A61B 2034/2048; A61B 2034/2055; A61B 2034/2057; A61B 2034/305; A61B 2090/064; A61B 17/1764; A61F 2/38; A61G 13/00
See application file for complete search history.

(56) References Cited

U.S. PATENT DOCUMENTS 3,766,384 A * 10/1973 Anderson .......... A61G 13/0036
378/209
4,979,949 A * 12/1990 Matsen, III ............ A61B 17/15
606/53

(Continued)

*Primary Examiner* — Robert G Santos
*Assistant Examiner* — Rahib T Zaman
(74) *Attorney, Agent, or Firm* — Schwegman Lundberg & Woessner, P.A.

(57) ABSTRACT

Examples of systems and methods for performing an orthopedic knee arthroplasty surgery with a robotic arm are generally described herein. A method may include awakening, using a robotic controller, a robotic arm from a parked mode to a surgical procedure mode. Moving, using the robotic controller, the robotic arm to a specified position to aid in the surgical procedure. The method may further include initiating, using the robotic controller, the surgical procedure by activating the robotic arm. In some examples, the robotic arm may be connected to a robotic base located between a first leg support configured to support a first leg of the patient during the surgical procedure and a second leg support configured to support a second leg of the patient during the surgical procedure.

20 Claims, 9 Drawing Sheets

(51) Int. Cl.
 A61B 17/17 (2006.01)
 A61B 90/00 (2016.01)

(56) References Cited

U.S. PATENT DOCUMENTS

| | | | | |
|---|---|---|---|---|
| 5,007,912 | A * | 4/1991 | Albrektsson | A61B 17/6425 |
| | | | | 128/882 |
| 6,378,149 | B1 * | 4/2002 | Sanders | A61B 6/0442 |
| | | | | 378/209 |
| 7,152,261 | B2 * | 12/2006 | Jackson | A61G 13/0036 |
| | | | | 5/600 |
| 7,947,006 | B2 * | 5/2011 | Torrie | A61G 13/1295 |
| | | | | 602/32 |
| 8,826,474 | B2 * | 9/2014 | Jackson | A61B 6/0407 |
| | | | | 5/611 |
| RE46,032 | E * | 6/2016 | Torrie | A61G 13/0036 |
| 9,814,411 | B2 * | 11/2017 | Branch | A61B 5/1121 |
| 10,292,774 | B2 * | 5/2019 | McDonell | A61B 34/30 |
| 10,292,887 | B2 * | 5/2019 | Kang | A61B 34/30 |
| 10,383,578 | B2 * | 8/2019 | Branch | A61B 5/4528 |
| 10,441,366 | B2 * | 10/2019 | Tabandeh | A61B 34/30 |
| 10,582,971 | B2 * | 3/2020 | Amiot | A61B 17/00234 |
| 2004/0133979 | A1 * | 7/2004 | Newkirk | A61F 5/3761 |
| | | | | 5/600 |
| 2004/0133983 | A1 * | 7/2004 | Newkirk | A61G 13/0036 |
| | | | | 5/624 |
| 2008/0132897 | A1 * | 6/2008 | Livorsi | A61B 17/154 |
| | | | | 606/88 |
| 2012/0046540 | A1 * | 2/2012 | Branch | A61B 5/4566 |
| | | | | 600/415 |

* cited by examiner

ROBOTICALLY-ASSISTED KNEE ARTHROPLASTY SUPPORT SYSTEMS AND METHODS

CLAIM OF PRIORITY

This application claims the benefit of U.S. Provisional Patent Application Ser. No. 62/610,064, filed on Dec. 22, 2017, the benefit of priority of which is claimed hereby, and which is incorporated by reference herein in its entirety.

BACKGROUND

The use of robotics in surgery is on the rise. Total and partial knee arthroplasty surgeries are performed over half a million times a year in the United States. In some cases, the surgeries are performed with assistance from a surgical robot. As the presence of robots and other equipment in the operating room increases, the available space to move in the same operating room decreases.

During robotically assisted surgeries, optical trackers are used to allow sensors or cameras to detect and track objects, such as anatomy of a patient, an instrument, or the surgical robot to aid in performing the surgery. In some situations, a crowded operating room can lead to optical trackers on the patient becoming blocked by people or objects maneuvering around the robot, or by the surgical robot itself. During some surgeries, the surgical robot and the surgeon are forced to compete for space or work from awkward angles or positions.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2 also shows a robot position and a surgeon position, in accordance with at least one example.

DETAILED DESCRIPTION

As discussed above, the use of robotics in surgery is on the rise. As the presence of robots and other equipment in the operating room increases, the available space in the operating room decreases. In particular, total and partial knee arthroplasty surgeries are performed over half a million times a year in the United States. While robotically assisted surgery is preferred by some surgeons, the combination of surgical robots and surgical tables may result in a crowded and suboptimal operating room layout for knee surgery.

The robot may obstruct portions of a surgical field, detracting from the robot's benefit to the surgeon. The robot, placed side-by-side with the surgeon, or across the patient from the surgeon, leaves little room for the surgical team to move around or work, and little room for instrument trays or anesthesia equipment. This crowded arrangement not only makes it difficult for the surgeon to perform the surgery, but also makes it difficult for the robot to assist the surgeon. For example, in some situations, a crowded operating room, may lead to optical trackers on the patient becoming blocked by people or objects maneuvering around the robot.

Systems and methods for supporting a patient during a surgical orthopedic knee procedure and for performing the procedure are described herein. The systems and methods provide space-saving patient supports and surgical robot arrangements. Examples described herein include support systems that may accommodate the surgical robot while locating the patient's leg in a proper position for the surgical orthopedic knee procedure. Such arrangements of the patient support and the surgical robot improve access to a surgical site for the surgeon and the surgical robot.

While some examples and figures described herein relate to specific examples, such as total or partial knee arthroplasty, many of the techniques described herein may be used on hip arthroplasty, shoulder repair or replacement procedures, other orthopedic implant procedures, or the like.

Figure 1A:
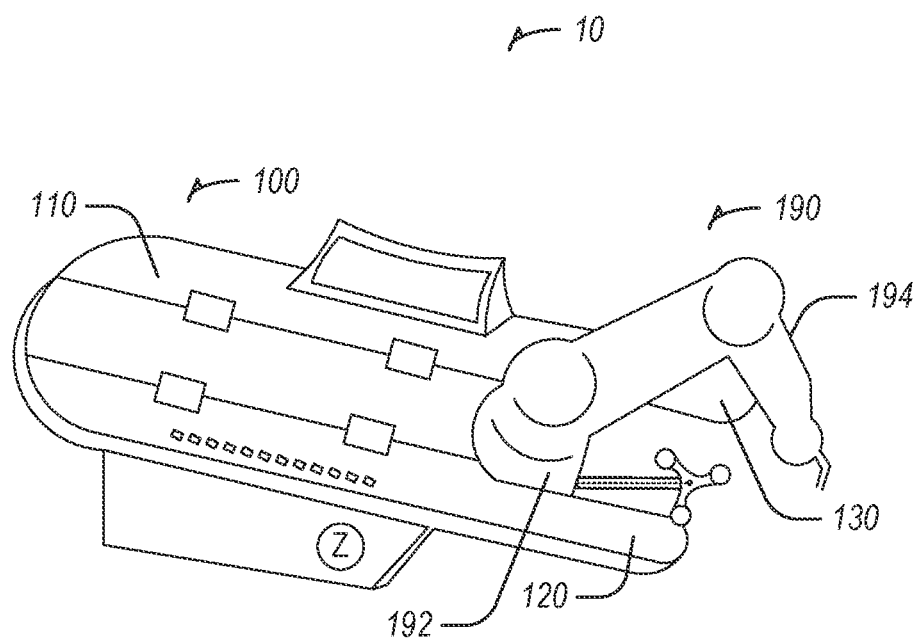
FIG. 1A illustrates a support system and a robot, in accordance with at least one example.

FIG. 1A illustrates a surgical field 10 in accordance with some embodiments. The surgical field 10 of FIG. 1A shows a support system 100 including a body support 110, a first leg support 120, a second leg support 130 and a surgical robot 190 having a robotic arm support 192. The robotic arm support 192 may be positioned proximate the first and second leg supports 120, 130 to support a robotic arm 194 of a surgical robot 190 (hereinafter, robot).

As shown, the first leg support 120 may be located to a first side of the robotic arm support 192, and the second leg support 130 may be located to a second side of the robotic arm support 192. In other words, the first and second leg supports 120, 130 may be located on opposite sides of the robotic arm support 192, or opposite sides of the robotic arm. Features of the surgical field 10 described herein may improve access to the surgical site by creating a less crowded space around the lateral sides of the patient.

Figure 1B:
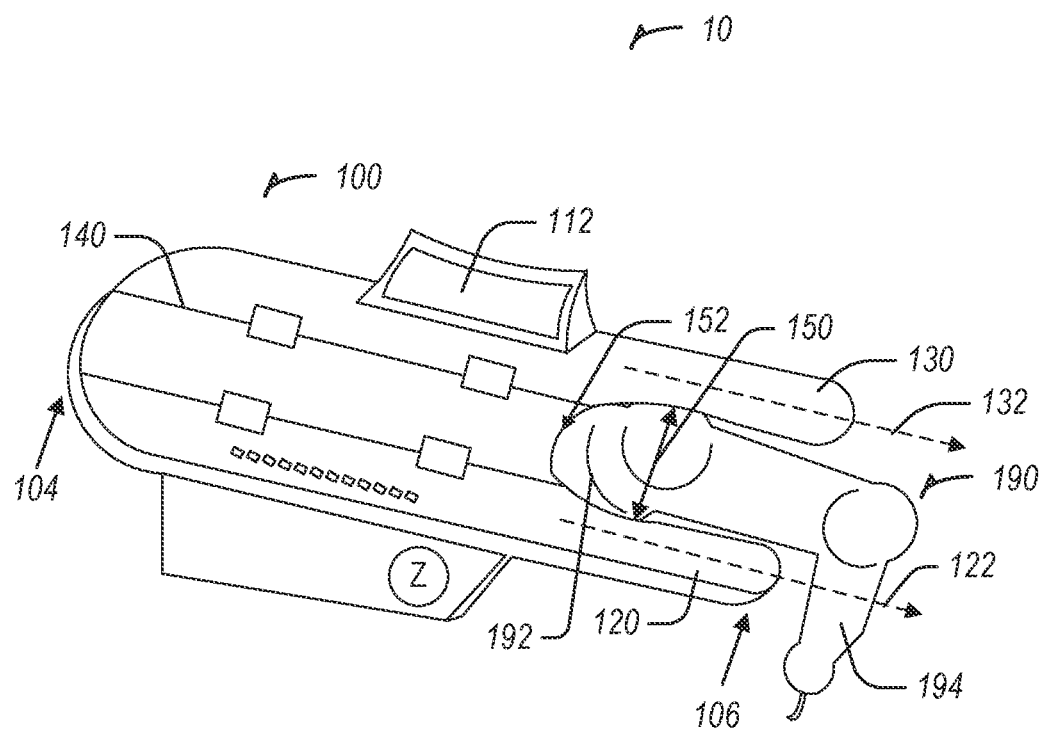
FIG. 1B illustrates the support system and the robot of FIG. 1A with the robot positioned in a parked mode, in accordance with at least one example.

FIG. 1B further illustrates the surgical field 10 including the support system 100 and the robot 190 of FIG. 1A. However, in FIG. 1B, the robotic arm 194 is shown positioned in a parked mode, in accordance with at least one example. In the parked mode, the robotic arm 194 may be trucked under the primary surface of the support system 100, which allows the support system 100 to function more closely to a standard surgical support table. In some examples, the robotic arm 194 can be parked fully under the support system 100. In certain examples, the gap may be filled with an insert or similar structure to allow the support system 100 to fully function as a standard surgical table.

Figure 2:
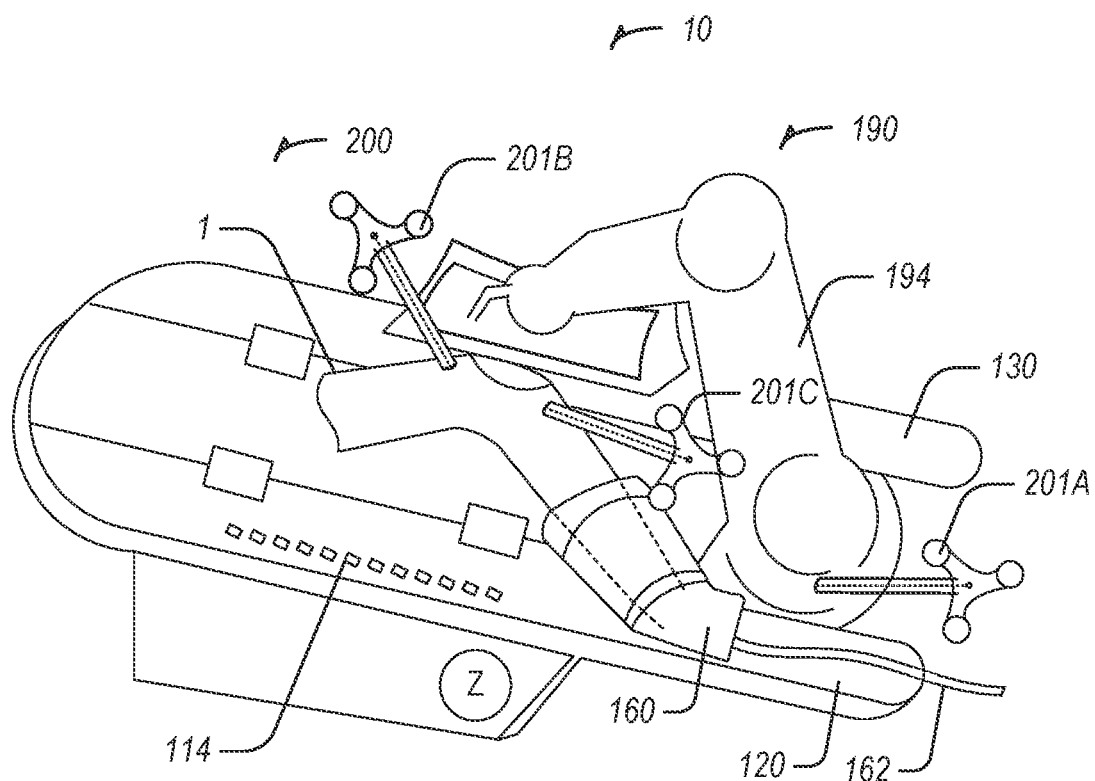
FIG. 2 illustrates a support system and robot including a patient placed on the support system, with the robot positioned in a surgical procedure mode, in accordance with at least one example.

FIG. 2 further illustrates a support system 200 and includes a portion of a patient (e.g., leg 1) placed on the support system 200 with the robotic arm 194 positioned in a surgical procedure mode. In the surgical procedure mode, the robotic arm 194 may be configured to perform a portion of a surgery, in accordance with at least one example.

As shown in FIG. 2, the first leg support 120 may be configured to support a first leg 1 of the patient during a surgical orthopedic knee procedure on the first leg 1. Likewise, the second leg support 130 may be configured to support a second leg of the patient during the surgical orthopedic knee procedure. In the example of FIG. 2, surgery may or may not be performed on the second leg.

To eliminate the crowded space along the sides of a support system 100, 200 or 300, lateral of the patient 1, and to provide the surgeon better access to the surgical site, the robot may be supported from a position between the patient's legs. For example, the first leg support 120 and the second leg support 130 may be spaced apart to define a gap 150. The gap 150 may be shaped and sized such that at least a portion of the robot 190 is insertable into the gap 150. With the surgeon positioned laterally to a side of the patient, the robot 190 may assist the surgeon from the robot's position between the first leg support 120 and the second leg support 130. In this arrangement, the surgeon and the robot may be positioned on opposite sides of the first leg 1.

With reference to FIG. 1B, the gap 150 may be formed as a recess 152 in the support system 100. In FIG. 1B, the support system 100 may be a surgical table 102. The surgical table 102 may extend from a first end portion 104 configured to support a patient's head, to a second end portion 106 configured to support the patient's legs or feet. In some examples, and as shown, the recess 152 may extend inwards from the second end portion 106 of the surgical table 102 such that at least a portion of the robot 190 may be inserted into the recess 152. The portion of the robot 190 that the recess 152 accommodates may include the robotic arm 194, an upper portion of the robotic arm support 192, or a front profile of the robot 190 facing the surgical table 102. The recess 152 may be configured to allow insertion of the robot 190 into a region between the patient's lower legs (e.g., tibias), the knees or upper legs (e.g., femurs).

The recess 152 may include the gap 150 having a maximum width between the first leg support 120 and the second leg support 130. In some examples, the recess 152 may be between 3 and 36 inches, depending on the access needed for the robot 190. In some examples, such as when only the robotic arm 194 needs to extend upward through the recess 152, the maximum width of the gap 150 may range between 3 and 18 inches, or for a smaller robot 190, between 3 to 12 inches. In other examples where a portion of the robot arm support 192 or another portion of the robot 190 needs to extend into the recess, the maximum width may range between 6 to 36 inches or 12-36 inches. For smaller robots, the maximum width may be between 6-24 inches. Controlling the maximum width allows the patient to be properly positioned for a surgical procedure, such as knee arthroplasty surgery.

Also shown in FIG. 1B, the first leg support 120 may extend along a first longitudinal axis 122. Likewise, the second leg support 130 may extend along a second longitudinal axis 132. In some examples and as shown, the first and second longitudinal axes 122, 132 may be substantially parallel to each other. Substantially may be defined herein as the first and second axes 122, 132 being within ±10 degrees of parallel with each other.

In other example where a larger gap is desired, the first and second axes 122, 132 may intersect at an intersection angle therebetween. (For an example of intersection angle, see intersection angle θ FIG. 4). Alternative to being substantially parallel, or within 10 degrees of one another, suitable intersection angles (e.g., angle between first and second axes) may range between 10 and 70 degrees, or, to keep the patient's legs in a more suitable position for knee arthroplasty, the suitable intersection angle may range between 10 and 45 degrees. In some examples, intersection may range between 0 and 90 degrees, for example, to accommodate a larger robot.

In some examples, the support system 100, 200, or 300 may include a generally elongate (e.g., generally rectangular) surgical table form. The gap 150 may be formed as a recess in the generally elongate surgical table.

The support system may include functional features such as a display 112. In some examples, the display may be a removable display 112 that may be attached or removed as needed, such as by a snap-in or other fastening feature. In some examples, the display 112 may be attached to compatible coupling features on either side of the support system 100, 200, or 300. This allows the surgeon to easily view the display 112 on the opposite side of the support system 100, 200, or 300 from the surgeon, depending on which of the legs is undergoing the surgical procedure.

The support system 100 may include moveable portions 140 to allow part of the support system 100, 200, or 300 to be moved out of the way or extended. In the examples shown in FIG. 1A-1B, 2, or 3, the movable portions 140 may be hinged so that the sides of the support system 100 fold up or down. In other examples, the movable portions 140 may slide relative to other parts of the support system 100, 200, or 300, such as sliding under another portion of the support system 100, 200, or 300.

FIG. 2 shows the support system 200 including a cuff 160 that may be used to support the first leg 1 during surgery. In some examples, the cuff 160 may be an inflatable pneumatic cuff. A benefit of an inflatable pneumatic cuff is that it may support the leg without the surgeon driving a pin into the leg 1. The cuff 160 may be coupled to the first leg support 120 and may hold the first leg 1 stationary while still allowing movement of the first leg 1 as needed by actuating pneumatics.

The cuff 160 may be operated via a pneumatic line 162 (partially shown). For example, the robot 190 may include the pneumatic line 162 such that is operably engaged with the pneumatic cuff 160 to inflate the pneumatic cuff 160. For example, at least a portion of the pneumatic line 162 may be coupled to or located within the robot 190, such as the robotic arm support 192 or the robotic arm 194. However, in some examples, the pneumatic line 162 may be external of the robotic arm support 192 or the robotic arm 194. In some examples, the pneumatic line 162 may be coupled to or located within any portion of the support system 200. The pneumatic cuff 160 may be used to hold the leg 1 in place during a soft tissue balancing test or may perform a soft tissue balancing test, such as by applying a force to the leg 1.

In an example, one or more optical trackers (e.g., 201A-201C) may be used to track various objects within the surgical field 10. For example, a first optical tracker 201A may be used to track the robotic arm 194 (e.g., to establish a static location of the robotic arm 194 within the surgical field 10, which may also be used as a reference location). The location of the robotic arm 194 within the tracking system using the first tracker 201A may allow for coordinate transfer from a coordinate system for the robotic arm 194 (which, for example, may be tracked using internal robotic sensors, such as a magnetoscope, gyroscope, accelerometer, using servo force output information, or the like) to an optical tracking coordinate system. For example, the location of the first tracker 201A may be a location commonly known to both coordinate systems. A second optical tracker 201B may be located on the femur of the patient 1 and a third optical tracker 201C may be located on the tibia of the patient 1. The second and third optical trackers 201B-201C may allow for tracking aspects of the knee, for example during a knee arthroplasty procedure, a soft tissue balancing test, or the like. Additional optical trackers may be used to track instruments or tools used during a procedure, or the like.

To determine positioning of the patient and to determine corresponding movements to be performed by the robot, the support system may include one or more sensors 114. In an example, the one or more sensors 114 may include table mounted controls. In an example, the one or more sensors 114 may be activated with a knee of the surgeon. The one or more sensors 114 may take the place of a pedal on the floor which may be used with current systems. Floor pedals are challenging to use since they move and are often not conveniently located to step on during a procedure. In another example, the one or more sensors 114 may be used to assess weight or force exerted by the robot 190, the surgical leg 1 or both. The one or more sensors 114 may be used to monitor the operative field (e.g., using infrared sensors or other location sensors to output locations of objects, such as the robot 190 or the leg 1).

Figure 3:
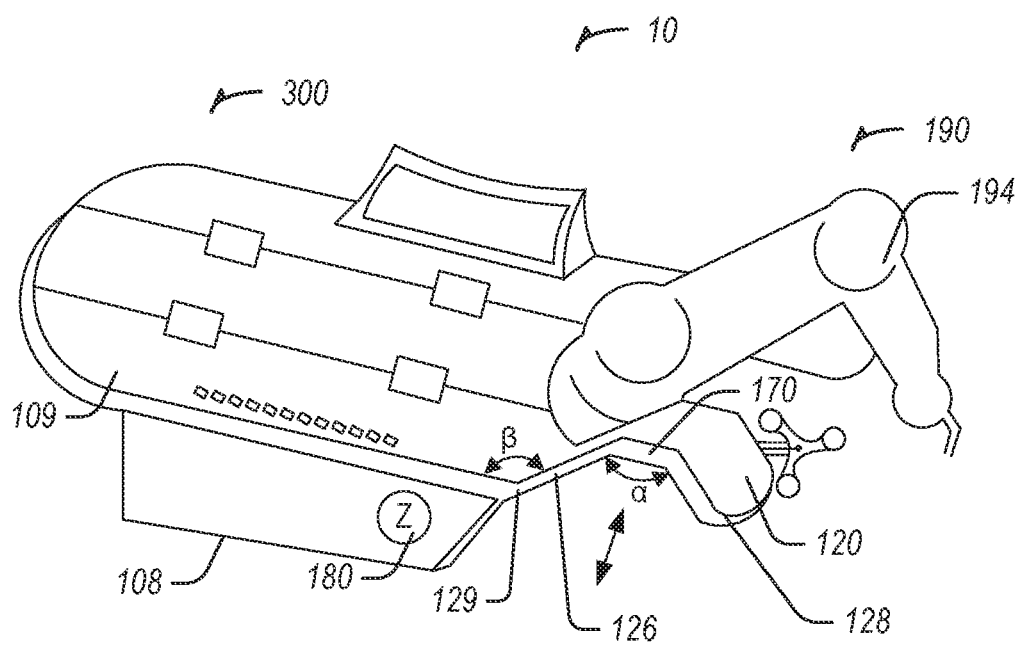
FIG. 3 illustrates a support system and the robot with a first leg support adjusted at an articulation portion, in accordance with at least one example.

FIG. 3 illustrates a support system 300 and a robot. The first leg support 120 is shown adjusted at an articulation portion 170. The articulation portion 170 may be configured to aid the surgeon in assessing knee flexion and performance of the soft tissue surrounding the knee. Instead of, or in addition to the surgeon pulling on the leg to assess soft tissue performance in the knee, the surgeon may perform an articulation test using the articulation portion 170. The first leg support may include an articulation portion 170 configured to be adjusted up or down relative to the first leg support 120. The patient may be positioned on the support system 300 with the patient's knee joint positioned near the articulation portion 170.

The articulation portion 170 may not be exactly at the knee joint, but instead may support the first leg 1 between the knee joint and the mid-thigh, proximal to the knee joint. As described herein, the patient 1 may be defined as being sized between a 5th percentile to $95^{th}$ percentile sized human.

To perform a soft tissue balancing test (e.g., a pull test) such as to determine balancing in knee ligaments during a knee arthroplasty, the first leg support 120 may be adjustable against gravity relative to the second leg support 130 to induce motion in the first leg 1. During motion or upon completion of the motion, a force or torque may be measured to evaluate balance in the soft tissue. In an example, the surgeon may determine balance after motion of the knee using the articulation portion 170. In another example, the force or torque may be measured using a sensor, such as within the robotic arm 194. In yet another example, the soft tissue balancing may be performed by causing the articulation portion 170 to raise the knee of the leg 1 to a specified angle, height, or force. A gap balance may be measured (e.g., difference in gap at a lateral and medial portion of the knee joint) or a tension may be measured (e.g., a difference in tension between lateral and medial soft tissue, such as ligaments). The articulation portion 170 may be arranged to perform the articulation test as a lift test (raising the knee) or a drop test (raising the leg 1 and dropping the knee). In performing either test, the knee joint may be bent to an articulation angle α, during which, an assessment of knee performance may be made.

Both the lift test and drop test may be understood with reference to FIG. 3. To perform the lift test, a upper first leg support 126 may be lifted (e.g., by pivoting about a hip pivot 129. When the upper first leg support 126 is pivoted about the hip pivot 129, the femur of the patient may be lifted and supported, for example, at a hip angle β. Suitable hip angles β may include about a 90 degree angle. Other angles may be specified by the surgeon preoperatively or intraoperatively. In some examples, the hip angle β may range between 45 and 135 degrees. The range may be adjusted based on the flexibility of the patient, or other patient specific parameters.

Both the upper 126 and a lower first leg support 128 (and thus both the femur and tibia) may be pivoted about the hip pivot 129 together. Once lifted, while being lifted, or after being lifted, the knee performance may be evaluated by pivoting the lower first leg support 128 to lower the patient's tibia to induce an articulation angle α. The articulation angle α is created by rotating the lower first leg support 128 (e.g., tibia) relative to the upper first leg support 126 (e.g., femur, thigh) at the articulation portion 170.

In some examples, the lifting or other motion may be performed by an actuator that is connected to the table or is under control of the robot, or is actuatable by the robotic arm 194. The articulation portion 170, or another portion of the support system 300, or the robot 190 may include a force sensor to measure force. The measured force may be used to determine the amount of force on a particular portion of the first leg 1 of the patient, such as the knee joint. In some examples, a change in force in a mid-operative or post-operative state may be compared to a pre-operative state.

In other words, in a lift test, to assess the knee performance, the force may be measured as the thigh is lifted and supported at a certain height (e.g., while the upper first leg support is raised to create a particular articulation angle α at the knee joint). The soft tissue forces may be determined using the force value that is required to raise the thigh and rotate to the articulation angle α, such as about 90 degrees. Other angles may be specified by the surgeon preoperatively or intraoperatively. In some examples, the articulation angle α may range between 45 and 135 degrees. The range may be adjusted based on the flexibility of the patient, or other patient specific parameters.

In the drop test example, the articulation portion 170 may be configured to drop the knee to allow a tibia of the first leg of the patient to drop and the performance of the knee to be assessed. In the drop test, the upper first leg portion 126 does not necessarily need to pivot at the hip pivot 129 and may remain substantially aligned with the body support 110, or rotated only a small angle β, such as between 10 and 20 degrees. In the drop test, the lower first leg portion 128 may be allowed to pivot (e.g., rotate, drop) to an angle α of about 90 degrees or more. This allows the tibia of the patient to drop and then the surgeon is able to assess flexion and soft tissue performance. Like the lift test, the assessment may include measuring the amount of force on a portion of the first leg 1 such as the knee joint. Measuring force may include determining a change in force in a mid-operative or post-operative state compared to a pre-operative state. In some examples, the articulation angle α may range between 45 and 135 degrees. Other angles may be specified by the surgeon preoperatively or intraoperatively.

Rather than measuring force, or in addition to measuring force, in other examples, the assessment using the articulation portion 170 may be a visual or tactile assessment by the surgeon using the motion induced by the articulation portion 170. Similar to the lift test, in the drop test, the articulation point may be near the knee joint itself, or anywhere between the knee and the mid-thigh, proximal to the knee joint.

To actuate features of the support system 300, such as actuating the articulation portion 170, or the robot 190 (e.g., to perform a portion of a surgical procedure, such as a soft tissue balancing test), a knee-activated actuator 180 may be activated. The knee-activated actuator 180 may be positioned between a base 108 of the support system 300 and a support surface 109 of the support system 300. In some examples, the knee-activated actuator 180 may be positioned at least 12 inches above the base 108 of the support system 300 that is configure to be in contact with a floor. In some examples, the knee-activated actuator 180 may be positioned between 12 and 36 inches above the base 180 of the support system 300. The knee-activated actuator 180 may be height adjustable to accommodate surgeons of different sizes.

The use of a knee-activated actuator 180 frees up the surgeon's hands to do other work. The knee-activated actuator 180 may reduce the chances of a surgeon being unable to find an actuator, such as over a foot activated actuator (which may not be fixed with respect to the support system 300 and thus may move or become lost or stuck during a procedure). In some examples, the knee-activated actuator 180 may be a kick/knee panel on the support system 300 including a pressure sensor to determine when the knee-activated actuator has been actuated (which may include requiring a sufficient force to prevent accidental activation). The motion to activate may be inward, upward, downward or sideways, a combination thereof, or the like. The knee-activated actuator 180 may be a button, a lever, a sensor, such as a motion sensor, or any other type of actuator that may be activated by the knee, upper leg (e.g., thigh) or lower leg (e.g., shin or calf) of the surgeon. In an example, the motion sensor may detect a gesture, such as a knee moving back and forth, up and down, etc., to activate. In some examples, a foot activator may be substituted or provided in addition to the knee-activated actuator 180.

Figure 4:
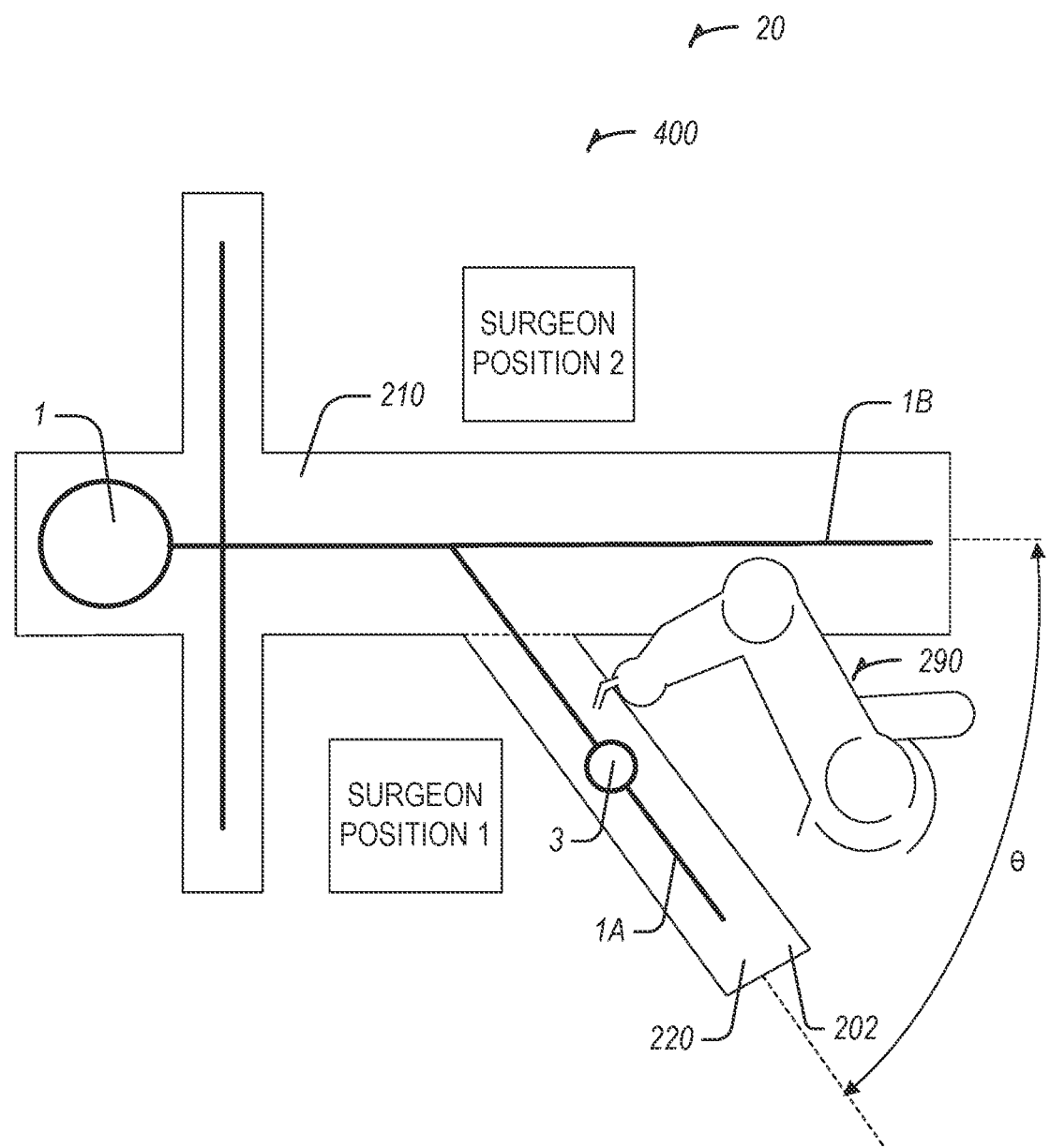
FIG. 4 illustrates a top view schematic of a patient positioned on a support system. The support system including a surgical table and a surgical table adapter.

FIG. 4 illustrates a top view schematic of a surgical field 20. The patient 1 is shown positioned on a support system 200 including a surgical table 210 and a surgical table adapter 210. FIG. 4 also shows a robot 290 position and two possible surgeon positions, in accordance with at least one example.

The support system of FIG. 4 may include a surgical table adapter 202 for supporting a portion of a patient during a surgical orthopedic knee procedure. The surgical table adapter 202 may be coupled to a surgical table 210 (e.g. a body support). The surgical table adapter 202 may support one of the legs 1A, 1B such that the robot 290 may be positioned in between first and second legs 1A, 1B of the patient. The surgical table adapter 202 may include a first leg support 220. With the surgical table adapter 202 supporting the first leg, the remaining portion of the patient, including the second leg 1B, may be supported by the surgical table 210.

With the robot 290 positioned between the patient's legs 1A, 1B, the surgeon may work from surgeon position 1. With the surgeon placed in surgeon position 1, both the robot 290 and the surgeon are able to access the knee joint 3 from a position lateral of the knee joint 3, opposite one another. Alternatively, the robot 290 and the surgeon position 1 or 2 may be reversed. Surgeon position 2 may be an alternate location for the surgeon or any personnel assisting the surgeon in position 1.

To accommodate the robot 290, the surgical table adapter may be configured to create an angle θ between the patient's legs 1A, 1B. Suitable angle θ may be between 10 and 70 degrees, or, to keep the patient's legs 1A, 1B in a more suitable position for knee arthroplasty, the suitable intersection angle may range between 10 and 45 degrees. In some examples, intersection may range between 0 and 90 degrees, for example, to accommodate a larger robot 290.

In some examples, the first leg support 220 may be configured to be stored under the surgical table 210 (e.g., body support). For example, the first leg support 220 may slide into or under, or fold relative to the surgical table 210. In other words, the surgical table adapter 202 may be separate from the surgical table 210, or may be storable in a compact form together with the surgical table 210.

To eliminate movement between the surgical table adapter 202 and the surgical table 210 and the robot 290, coupling features may be provided. Example coupling features are described with reference to FIG. 5.

Figure 5:
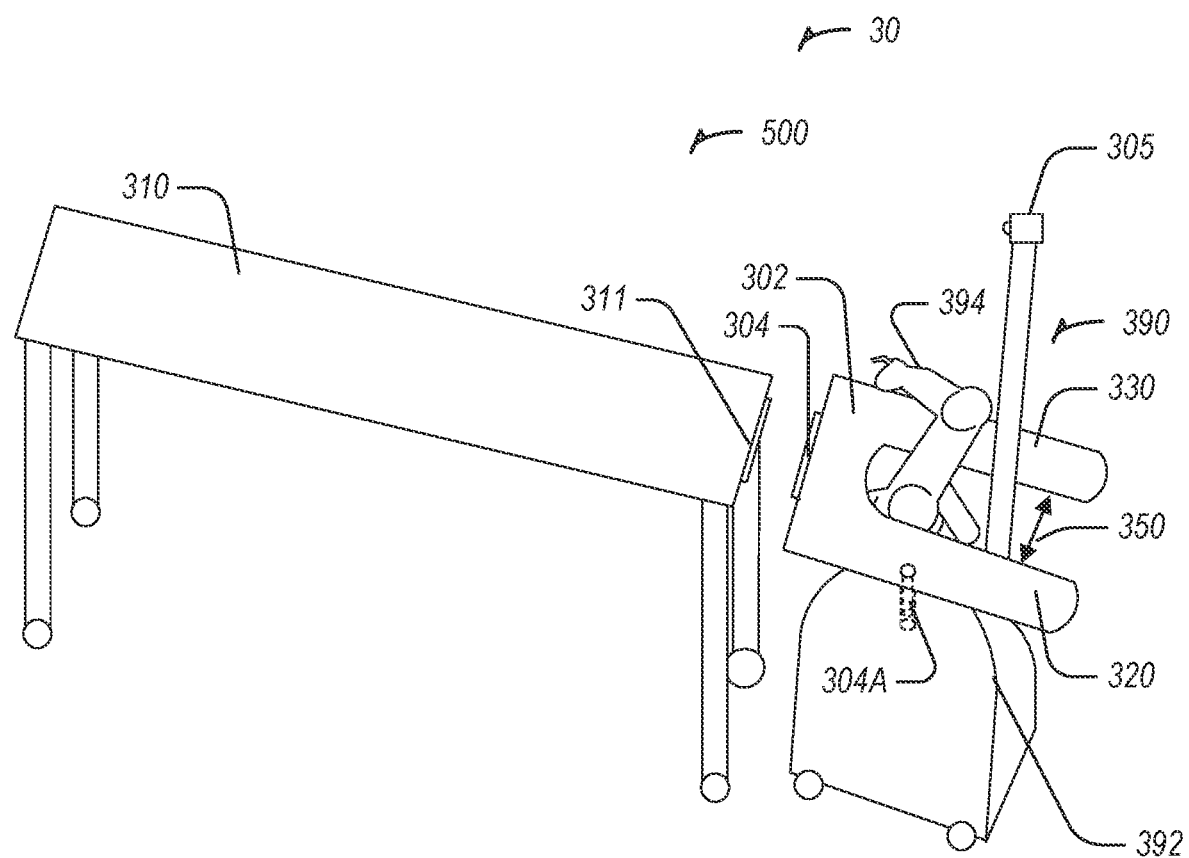
FIG. 5 illustrates a perspective view of a surgical table as well as a robot including patient leg supports, in accordance with at least one example.

FIG. 5 illustrates a perspective view of a surgical field 30 including a support system 300 having a surgical table 310, a surgical table adapter 302 and a robot 390 in accordance with at least one example.

The surgical table adapter 302 may be configured to support a portion of a patient during a surgical orthopedic knee procedure. The surgical table adapter 302 may include a first leg support 320, a second leg support 330 and a coupling mechanism 304. The first and second leg supports 320, 330 may include features of the first and second leg supports 120, 130, 220, 230 described with respect to any of the example support systems of FIGS. 1A-1B, 2, 3, and 4.

The first leg support 320 may be configured to support a first leg of the patient during the surgical orthopedic knee procedure on the first leg. Likewise, the second leg support 330 may be configured to support a second leg of the patient during the orthopedic knee procedure. The first and second leg supports 320 and 330 may be joined to each other.

The first and second leg supports 320, 330 may be spaced apart to define a gap 350 such that at least a portion of a robot 390, such as a robotic arm support 392 or robotic arm support 394 is insertable into the gap 350 to perform a portion of the surgical orthopedic knee procedure (e.g., FIG. 1B). As shown in FIG. 5, the gap 350 may be configured to fit a front profile of the robotic arm 394.

In some examples, the robotic arm support 392 is located below the surgical table adapter 302 and the robotic arm 394 is insertable into the gap 350 from below.

The coupling mechanism 304 may secure the surgical table adapter 302 to the surgical table 310 in order to provide stable support to the patient. It may be undesirable for the surgical table adapter 302 to move relative to the surgical table 310 during portions of the surgical procedure.

The coupling mechanism 304 may be configured to couple the surgical table adapter 302 to a surgical table 310. The coupling mechanism 304 may be provided in various forms. Each of the surgical table adapter 302 and the surgical table 310 may include features or surfaces to facilitate coupling to one another. Example coupling mechanisms 304 may be provided in the form of a bolted connection, a clamp style connection, a pin and hole connection, a hitch type connection, a mechanical or electrically operated locking mechanism, or a magnetic connection, among others. The surgical table 310 may include a complementary coupling mechanism 311 or other feature that the coupling mechanism 304 may be coupled to.

In addition to the coupling mechanism 304 between the surgical table adapter 302 and the surgical table 310, other securing features may be provided in the support system 300.

For example, to provide a secure connection between the robot 390 and other elements of the support system 300, a robot coupling interface (es. 304, 304A) may be adapted to couple the robot 390 to the support system 300. In some examples, the robot 390 may be coupled to (e.g., is couplable to) the surgical table 310. In other examples, the robot 390 may be coupled to (e.g., couplable to) the surgical table adapter 302. Further, in some examples, the robot 390 may be coupled to both the surgical table 310 and the surgical table adapter 302. To facilitate coupling, the robot 390 may include a coupling feature corresponding to a coupling feature on the surgical table 310 or surgical table adapter 302. Example robot coupling interfaces may include a bolted connection, a clamp style connection, a pin and hole connection, a hitch type connection, a mechanical or electrically operated locking mechanism, or a magnetic connection, among others.

As shown in FIG. 5, the surgical table adapter 302 is coupled to the robot 390 with the surgical table adapter 302 being removably coupled to the surgical table 310. In some examples, the robot 390 may be removably coupled to the surgical table 310 (e.g., a body support table) instead of, or in addition to the surgical table adapter 302.

In some examples, an optical camera 305 may be affixed to at least one of the robotic arm support 392, the robotic arm 394, the first leg support 320, or the second leg support 330. The optical camera 305 may be configured to track optical trackers during at least a portion of the surgical orthopedic knee procedure. The tracking may be performed using the optical camera 305 with optical trackers affixed to a surgical tool, a surgical instrument, anatomy of the patient (e.g., a bone, such as the femur or tibia), the robot 390, the surgical table 310 or other objects within the surgical field 30. In an example, locating the optical camera 305 on the robot 390 or the robotic arm 394 may allow the tracking system to be moveable. In an example, locating the optical camera 305 on the robot 390 or the robotic arm 394 may allow the tracking system to know a location of a base of the robot 390 or the robotic arm 394, which may allow for transferring tracked object information or locations or robotic arm 394 location or information between coordinate systems, such as without needing an optical tracker on the robotic arm 394 or the robot 390.

Figure 6:
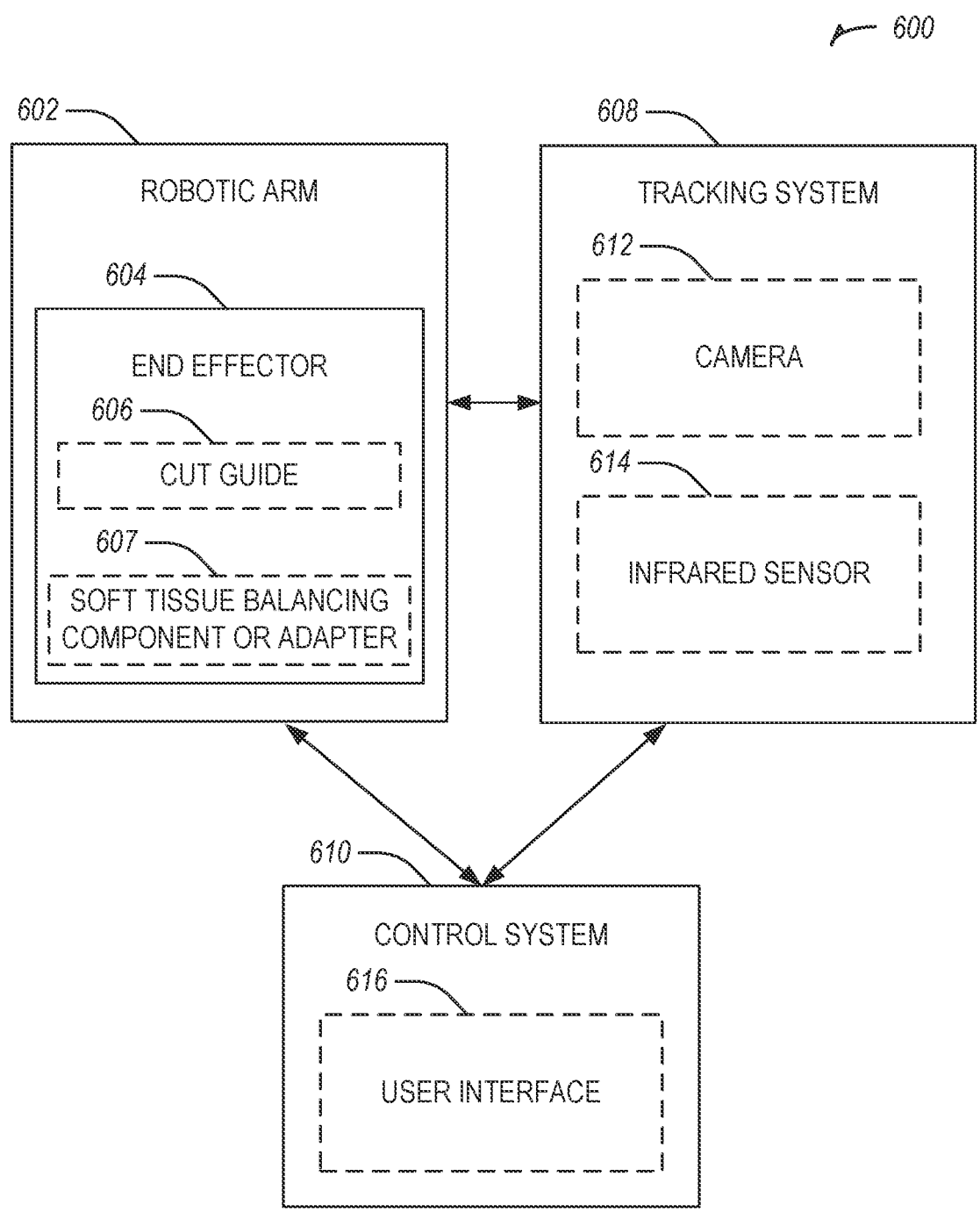
FIG. 6 illustrates a system for surgical tracking and control in an example.

FIG. 6 illustrates a system 600 for surgical tracking and control in accordance with some embodiments. The system 600 may include a robotic arm 602, a tracking system 608, and a control system 610.

The robotic arm 602 may include an end effector 604, optionally including a cut guide 606 or a soft tissue balancing component or adapter 607, either or both of which may be mounted on the end effector 604. The robotic arm 602 may be configured to allow interactive movement and controlled autonomous movement of the end effector 604. The cut guide 606 may be configured to guide a surgical instrument within a line or plane (e.g., a cutting device to cut a target object). The soft tissue balancing component or adapter 607 may be used to perform a soft tissue balancing test, such as a pull test, a push test, or the like.

The tracking system 608 may optionally include a camera 612 or an infrared sensor 614. The tracking system 608 may use the camera 612 or the infrared sensor 614 to track the robotic arm 602, the end effector 604, the cut guide 606, a target object, or the like. In an example, the tracking system 608 may be used to determine a position or an orientation of the cut guide 606. The position or the orientation may be determined relative to a coordinate system or relative to a target object. An example optical tracking device commonly used for this type of application is the Polaris Optical Tracking System from Northern Digital of Waterloo, Ontario, Canada. In an example, the camera 612 of the tracking system 608 may be affixed to a portion of the robotic arm 602 or a base of the robotic arm 602. The tracking system 608 may output tracking information (e.g., location of the end effector 604, a tool, anatomy of a patient, etc.).

The control system 610 may optionally include a user interface 616. In another example, the user interface 616 may be separate from the control system 610 or may be communicatively coupled to the control system 610. The control system 610 may be used to determine a zone occupied by the cut guide 606, such as using the position or the orientation of the cut guide, a target object, or a coordinate system. The zone may include a safety zone, an interaction zone, or a free-drive zone. In response to determining the zone is a free-drive zone, the control system 610 may permit interactive movement of the end effector 604 and prevent autonomous movement of the end effector 604. In response to determining the zone is an interactive zone, the control system 610 may permit interactive movement and autonomous movement of the end effector 604. The control system 610 may prevent interactive movement into the safety zone.

In an example, the control system 610 may establish the interaction zone using anatomical landmarks of the target object (e.g., a target bone) or identified locations of the target object (e.g., digitized locations). The tracking system 608 may determine a position or an orientation of a target object relative to the coordinate system. The position or the orientation of the cut guide 606 may be determined relative to the position or the orientation of the target object by the tracking system. In an example, the coordinate system is determined from the position or the orientation of the target object.

Figure 7:
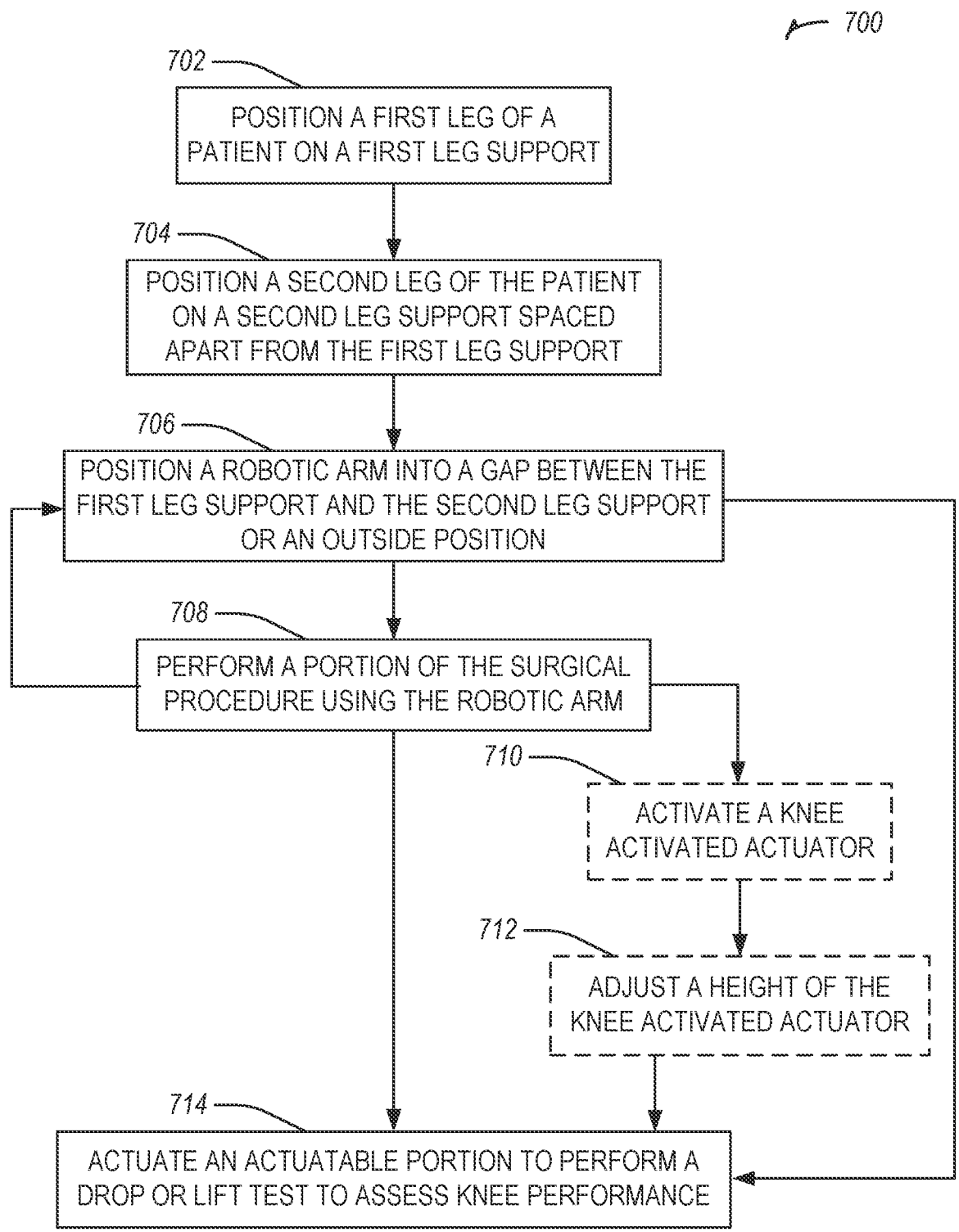
FIG. 7 illustrates a flow chart showing a technique for performing a surgical orthopedic knee procedure on a patient.

FIG. 7 illustrates a flow chart showing a technique 700 for performing a surgical orthopedic knee procedure on a patient. The illustrative technique 700 may be applied to any of the support systems 100, 200, 300, 400, 500, and surgery fields 10, 20, 30 described above. The illustrative technique 700 may also be applied to other support systems and surgery fields.

The technique 700 may include an operation 702 to position a first leg of a patient on a first leg support. Similar to operation 702, an operation 704 may include positioning a second leg of the patient on a second leg support. In operations 702 and 704, the first leg may be positioned in a spaced apart relationship from the second leg.

Technique 700 may further include an operation 706 to position a robotic arm into a gap between the first leg support and the second leg support. With the robotic arm in between the patient's first and second legs, the robot may be beneficially positioned to assist the surgeon in a surgical procedure. Optionally, operation 706 may be performed prior to any patient positioning operations. In such an example, the robotic arm may be parked out of the way to allow for easy patient positioning with the robot in place for the procedure to begin. In an example, a surgeon performing a procedure may occupy the gap between the first leg support and the second leg support. In this example, the robotic arm may be located at an outside position (i.e., lateral to one of the first or second legs), while the surgeon occupies the gap. The surgeon and the robotic arm may be interchangeably located in these positions (either in the gap or lateral to one of the two legs).

Operation 708 may include the robot performing a portion of the surgical procedure using the robotic arm. Suitable surgical procedures include robotically assisted knee arthroplasty. In an example, operation 708 may include both the robot and the surgeon performing the surgical procedure from positions lateral of the first leg but on opposite sides of the first leg. After operation 708, the technique 700 may include returning to operation 706, for example to reposition the robotic arm. In an example, the robotic arm may be located in the gap between the two leg supports for a first portion of a procedure or a first procedure (e.g., a knee arthroplasty on a knee of the first leg) and then moved to a position lateral to the second leg support to perform a second portion of a procedure or second procedure (e.g., a knee arthroplasty on a knee of the second leg). In another example, the robotic arm may remain within the gap, but rotate or move to perform a second portion of a procedure or a second procedure.

In an example, after performing a portion of the surgical procedure using the robotic arm in operation 708, the technique 700 may include optional operations 710 or 712. Optional operation 710 may include activating a knee-activated actuator located on a lateral side of the support component such as one of the previously described support systems 100, 200, 300, 400, or 500. In some examples, optional operation 712 may include adjusting a height of the knee-activated actuator. Optional operation 712 may be beneficial to accommodate users of various sizes. Adjusting the height of the knee-activated actuator makes it easier for shorter users to access the knee-activated actuator, or tall users to move the knee-activated actuator higher and more out of the way.

In an example, after operation 708, the technique 700 may include proceeding to operation 714, with or without optional operations 710 or 712 between. In another example, the technique 700 may include proceeding to operation 714 from operation 706. Operation 714 may include performing a pull or lift test by activating an actuatable portion such as an articulation portion (e.g., 170, FIG. 2), thereby lifting the first leg of the patient. Operation 714 may also include performing a drop test by activating an actuatable portion such as an articulation portion (e.g., 170, FIG. 2), thereby dropping at least a portion of the first leg of the patient.

Figure 8:
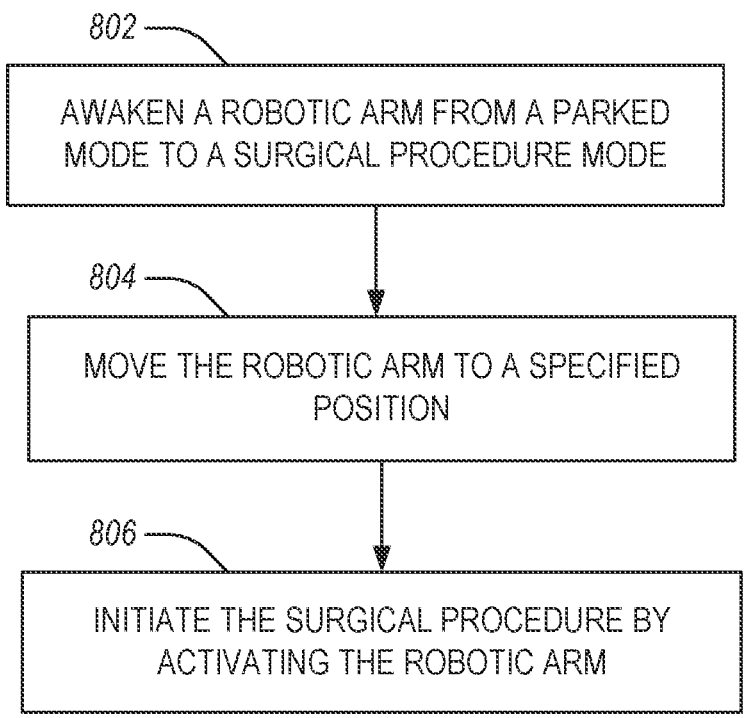
FIG. 8 illustrates a flow chart showing a technique for performing a surgical procedure with a robotic arm.

FIG. 8 illustrates a flow chart showing a technique 800 for performing a surgical procedure with a robotic arm. The illustrative technique 800 may be applied to any of the surgical robots 190, 290, 390, the support systems 100, 200, 300 and surgery fields 10, 20, 30 described above. The illustrative technique 800 may also be applied to other surgical robots, support systems and surgery fields.

The technique 800 may include an operation 802 to awaken a robotic arm from a parked mode (FIG. 1B) to a surgical procedure mode (FIG. 2) The awakening operation 802, may be performed using a robotic controller operably coupled to the robotic arm.

Operation 804 may include moving the robotic arm, using the robotic controller, to a specified position to aid in the surgical procedure. In some examples, as described herein, the robotic arm may be connected to a robotic base located between a first leg support and a second leg support. The first leg support configured to support a first leg of the patient and the second leg support configured to support the second leg support Operation 806 may include to initiate the surgical procedure by activating the robotic arm. Surgical procedures initiated in Operation 806 may include robotically assisted knee arthroplasty.

VARIOUS NOTES & EXAMPLES

Each of these non-limiting examples may stand on its own, or may be combined in various permutations or combinations with one or more of the other examples.

Example 1 is a support system for supporting a patient during a surgical orthopedic knee procedure, the support system comprising: a robotic arm support configured to support a robotic arm to perform a portion of the surgical orthopedic knee procedure; a first leg support located to a first side of the robotic arm support configured to support a first leg of the patient during the portion of the surgical orthopedic knee procedure; and a second leg support located to a second side of the robotic arm support opposite the first side, the second leg support configured to support a second leg of the patient during the portion of the surgical orthopedic knee procedure.

In Example 2, the subject matter of Example 1 includes, wherein the support system further comprises an optical camera affixed to one of the robotic arm support, the first leg support, or the second leg support, the optical camera configured to track optical trackers during the portion of the surgical orthopedic knee procedure.

In Example 3, the subject matter of Examples 1-2 includes wherein the first leg support is adjustable against gravity relative to the second leg support.

In Example 4, the subject matter of Examples 1-3 includes wherein the first leg support includes an articulation portion, the articulation portion configured to be adjusted up or down relative to the first leg support.

In Example 5, the subject matter of Example 4 includes wherein the first leg support includes a lower first leg support that is configured to drop to allow a tibia of the first leg of the patient to drop to perform a soft tissue drop test.

In Example 6, the subject matter of Examples 4-5 includes wherein the articulation portion is configured to be located proximal to the patient from a knee joint during a lift or drop test.

In Example 7, the subject matter of Examples 4-6 includes wherein the articulation portion is configured to lift a femur of the first leg of the patient to perform a soft tissue pull test.

In Example 8, the subject matter of Example 7 includes wherein the articulation portion is actuatable by the robotic arm.

In Example 9, the subject matter of Examples 4-8 includes wherein the articulation portion includes a force sensor to determine an amount of force on a portion of the first leg of the patient.

In Example 10, the subject matter of Examples 4-9 includes wherein the articulation portion is configured to raise the first leg such that a knee joint of the first leg is supported at a ninety degree angle.

In Example 11, the subject matter of Examples 1-10 includes wherein the support system further includes a knee-activated actuator at a position at least twelve inches above a portion of the support system in contact with a floor.

In Example 12, the subject matter of Examples 1-11 includes wherein the support system further includes a display screen.

In Example 13, the subject matter of Examples 1-12 includes wherein the first leg support further includes a pneumatic cuff to support the first leg.

In Example 14, the subject matter of Example 13 includes wherein the robotic arm support includes a pneumatic line that is operably engagable with the pneumatic cuff to inflate the pneumatic cuff.

In Example 15, the subject matter of Examples 1-14 includes wherein the first leg support extends along a first longitudinal axis, and wherein the second leg support extends along a second longitudinal axis, and where the first and second longitudinal axis are substantially parallel.

In Example 16, the subject matter of Examples 1-15 includes wherein the first leg support extends along a first longitudinal axis, and wherein the second leg support extends along a second longitudinal axis, and wherein the first and second longitudinal axis are between ten and forty-five degrees apart.

In Example 17, the subject matter of Examples 1-16 includes a recess having a recess width extending from the first leg support to the second leg support, and a maximum recess width is between six and twenty-four inches.

Example 18 is a surgical table adapter for supporting a patient during a surgical orthopedic knee procedure, the surgical table adapter comprising: a coupling mechanism for coupling the surgical table adapter to a surgical table; a first leg support configured to support a first leg of the patient during the surgical orthopedic knee procedure, a second leg support configured to support a second leg of the patient during the surgical orthopedic knee procedure; and wherein the first leg support and the second leg support are spaced apart to define a gap, such that a robotic arm of a surgical robot is insertable into the gap to perform a portion of the surgical orthopedic knee procedure.

In Example 19, the subject matter of Example 18 includes wherein the surgical table adapter further includes a robot coupling interface adapted to couple the surgical robot to the surgical table adapter when the surgical robot is positioned in the gap.

In Example 20, the subject matter of Example 19 includes wherein the first leg support is configured to be stored under the surgical table.

In Example 21, the subject matter of Examples 18-20 includes wherein the gap is configured to fit a front profile of the robotic arm.

In Example 22, the subject matter of Examples 18-21 includes wherein a robotic arm support for the robotic arm is located below the surgical table adapter, and wherein the robotic arm is insertable into the gap from below the surgical table adapter.

In Example 23, the subject matter of Examples 18-22 includes wherein the second leg support is joined to the first leg support.

In Example 24, the subject matter of Examples 18-23 includes an optical camera affixed to at least one of a robotic arm support, the robotic arm, the first leg support, or the second leg support, the optical camera configured to track optical trackers during at least a portion of the surgical orthopedic knee procedure.

In Example 25, the subject matter of Examples 18-24 includes wherein the first leg support includes an articulation portion, the articulation portion configured to be adjusted up or down relative to the first leg support.

In Example 26, the subject matter of Example 25 includes wherein the articulation portion is configured to drop to allow a tibia of the first leg of the patient to drop to perform a soft tissue drop test.

In Example 27, the subject matter of Examples 25-26 includes wherein the articulation portion is configured to be located proximal to the patient from a knee joint during a lift or drop test.

In Example 28, the subject matter of Examples 25-27 includes wherein the articulation portion is configured to lift a femur of the first leg of the patient to perform a soft tissue pull test.

In Example 29, the subject matter of Example 28 includes wherein the articulation portion is actuatable by the robotic arm.

In Example 30, the subject matter of Examples 25-29 includes wherein the articulation portion includes a force sensor to determine an amount of force on a portion of the first leg of the patient.

In Example 31, the subject matter of Examples 25-30 includes wherein the articulation portion is configured to raise the first leg such that a knee joint of the first leg is supported at a ninety degree angle.

In Example 32, the subject matter of Examples 18-31 includes wherein the surgical table adapter further includes a knee-activated actuator at a position between twelve and thirty-six inches above a portion of the surgical table or surgical table adapter in contact with a floor.

In Example 33, the subject matter of Examples 18-32 includes wherein the first leg support extends along a first longitudinal axis, and wherein the second leg support extends along a second longitudinal axis, and where the first and second longitudinal axis are substantially parallel.

In Example 34, the subject matter of Examples 18-33 includes wherein the first leg support extends along a first longitudinal axis, and wherein the second leg support extends along a second longitudinal axis, and wherein the first and second longitudinal axis are between ten and forty-five degrees apart.

In Example 35, the subject matter of Examples 18-34 includes wherein the gap is formed by a recess having a recess width extending from the first leg support to the second leg support, and a maximum recess width is between six and twenty-four inches.

Example 36 is a method for performing a surgical orthopedic knee procedure on a patient, the method comprising: positioning a first leg of the patient on a first portion of a support component, wherein the first leg is spaced apart from a second leg; positioning a robotic arm into a gap portion of the support component between the first leg and the second leg; and performing a portion of the surgical orthopedic knee procedure using the robotic arm.

In Example 37, the subject matter of Example 36 includes wherein performing the portion of the surgical orthopedic knee procedure includes performing a robotically assisted knee arthroplasty.

In Example 38, the subject matter of Examples 36-37 includes wherein performing the portion of the surgical procedure includes performing the portion of the surgical orthopedic knee procedure from a position lateral of the first leg.

In Example 39, the subject matter of Examples 36-38 includes activating a knee-activated actuator located on a side of the support component.

In Example 40, the subject matter of Example 39 includes adjusting a height of the knee-activated actuator.

In Example 41, the subject matter of Examples 36-40 includes activating an articulation portion of the support component to lift the first leg of the patient to perform a pull test.

In Example 42, the subject matter of Examples 36-41 includes activating an articulation portion of the support component to drop the first leg of the patient to perform a drop test.

Example 43 is a surgical table for supporting a patient during a surgical orthopedic knee procedure, the surgical table comprising: a first leg support configured to support a first leg of the patient during the surgical orthopedic knee procedure, a second leg support configured to support a second leg of the patient during the surgical orthopedic knee procedure; wherein the first leg support and the second leg support are spaced apart to define a gap, such that a surgical robot is insertable into the gap to perform a portion of the surgical orthopedic knee procedure; and a body support configured to support remaining portions of the patient.

In Example 44, the subject matter of Example 43 includes wherein the gap is formed as a recess in a rectangular surgical table.

In Example 45, the subject matter of Examples 43-44 includes wherein the gap is configured to fit a front profile of a robotic arm.

In Example 46, the subject matter of Examples 43-45 includes wherein the first leg support includes an articulation portion, the articulation portion configured to be adjusted up or down relative to the first leg support.

In Example 47, the subject matter of Example 46 includes wherein the articulation portion is configured to drop to allow a tibia of the first leg of the patient to drop to perform a soft tissue drop test.

In Example 48, the subject matter of Examples 46-47 includes wherein the articulation portion is configured to be located proximal to the patient from a knee joint during a lift or drop test.

In Example 49, the subject matter of Examples 46-48 includes wherein the articulation portion is configured to lift a femur of the first leg of the patient to perform a soft tissue pull test.

In Example 50, the subject matter of Example 49 includes wherein the articulation portion is actuatable by a robotic arm of the surgical robot.

In Example 51, the subject matter of Examples 46-50 includes wherein the articulation portion includes a force sensor to determine an amount of force on a portion of the first leg of the patient.

In Example 52, the subject matter of Examples 46-51 includes wherein the articulation portion is configured to raise the first leg such that a knee joint of the first leg is supported at a ninety degree angle.

In Example 53, the subject matter of Examples 43-52 includes inches above a portion of the support system in contact with a floor.

In Example 54, the subject matter of Examples 43-53 includes wherein the first leg support further includes a pneumatic cuff to support the first leg.

In Example 55, the subject matter of Example 54 includes wherein the pneumatic cuff is inflated via a pneumatic line operably coupled to the pneumatic cuff from a robotic arm support of the surgical robot.

In Example 56, the subject matter of Examples 43-55 includes wherein the first leg support extends along a first longitudinal axis, and wherein the second leg support extends along a second longitudinal axis, and where the first and second longitudinal axis are substantially parallel.

In Example 57, the subject matter of Examples 43-56 includes wherein the first leg support extends along a first longitudinal axis, and wherein the second leg support extends along a second longitudinal axis, and wherein the first and second longitudinal axis are between ten and forty-five degrees apart.

In Example 58, the subject matter of Examples 43-57 includes wherein the gap is formed as a recess and has a recess width from the first leg support to the second leg support, and a maximum recess width is between six and twenty-four inches.

Example 59 is a method for performing a surgical procedure with a robotic arm, the method comprising: awakening, using a robotic controller, the robotic arm from a parked mode to a surgical procedure mode; moving, using the robotic controller, the robotic arm to a specified position to aid in the surgical procedure, the robotic arm connected to a robotic base located between a first leg support configured to support a first leg of a patient during the surgical procedure and a second leg support opposite the first leg support, the second leg support configured to support a second leg of the patient during the surgical procedure; and initiating, using the robotic controller, the surgical procedure by activating the robotic arm.

Example 60 is at least one machine-readable medium including instructions that, when executed by processing circuitry, cause the processing circuitry to perform operations to implement of any of Examples 1-59.

Example 61 is an apparatus comprising means to implement of any of Examples 1-59.

Example 62 is a system to implement of any of Examples 1-59.

Example 63 is a method to implement of any of Examples 1-59.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A support system to support at least a portion of a patient during a surgical orthopedic knee procedure and to support a robotic arm to perform a portion of the surgical orthopedic knee procedure, the support system comprising:
   a robotic arm support configured to support the robotic arm;
   a first leg support coupled to the robotic arm support and located to a first side of the robotic arm support, the first leg support configured to support a first leg of the patient during the portion of the surgical orthopedic knee procedure;
   a second leg support coupled to the robotic arm support and located to a second side of the robotic arm support opposite the first side, the second leg support configured to support a second leg of the patient during the portion of the surgical orthopedic knee procedure.

2. The support system of claim 1, wherein the support system further comprises an optical camera affixed to one of the robotic arm support, the first leg support, or the second leg support, the optical camera configured to track optical trackers during the portion of the surgical orthopedic knee procedure.

3. The support system of claim 1, wherein the first leg support includes a lower first leg support that is configured to drop to allow a tibia of the first leg of the patient to drop to perform a soft tissue drop test.

4. The support system of claim 1, wherein the first leg support includes an articulation portion, the articulation portion configured to be adjusted up or down relative to the first leg support, wherein the articulation portion is actuatable by the robotic arm.

5. The support system of claim 1, wherein the first leg support includes an articulation portion, the articulation portion configured to be adjusted up or down relative to the first leg support wherein the articulation portion includes a force sensor to determine an amount of force on a portion of the first leg of the patient.

6. The support system of claim 1, wherein the first leg support further includes a pneumatic cuff to support the first leg, and wherein the robotic arm support includes a pneumatic line that is operably engagable with the pneumatic cuff to inflate the pneumatic cuff.

7. A surgical table adapter for supporting a patient during a surgical orthopedic knee procedure that is performed at least in part by a robotic arm, the surgical table adapter comprising:
   a coupling mechanism configured to couple the surgical table adapter to a surgical table;
   a first leg support configured to support a first leg of the patient during the surgical orthopedic knee procedure;
   a second leg support configured to support a second leg of the patient during the surgical orthopedic knee procedure, and wherein the first leg support and the second leg support are spaced apart to define a gap configured to receive the robotic arm; and
   a coupling interface configured to couple the surgical table adapter to the robotic arm when the robotic arm is positioned in the gap.

8. The surgical table adapter of claim 7, wherein a robotic arm support for the robotic arm is located below the surgical table adapter, and wherein the robotic arm is insertable into the gap from below the surgical table adapter.

9. The surgical table adapter of claim 7, further comprising an optical camera affixed to at least one of a robotic arm support, the robotic arm, the first leg support, or the second leg support, the optical camera configured to track optical trackers during at least a portion of the surgical orthopedic knee procedure.

10. The surgical table adapter of claim 7, wherein the first leg support includes an articulation portion, the articulation portion configured to be adjusted up or down relative to the first leg support, wherein the articulation portion is configured to lift a femur of the first leg of the patient to perform a soft tissue pull test, wherein the articulation portion is actuatable by the robotic arm, wherein the articulation portion includes a force sensor to determine an amount of force on a portion of the first leg of the patient.

11. A surgical table for supporting a patient during a surgical orthopedic knee procedure involving a surgical robot, the surgical table comprising:
   a first leg support configured to support a first leg of the patient during the surgical orthopedic knee procedure,
   a second leg support configured to support a second leg of the patient during the surgical orthopedic knee procedure;
   wherein the first leg support and the second leg support are spaced apart to define a gap, such that the surgical robot can be received into the gap to perform a portion of the surgical orthopedic knee procedure;
   a body support configured to support remaining portions of the patient; and
   a knee-activated actuator, that when actuated, causes a portion of the surgical orthopedic knee procedure to be performed.

12. The surgical table of claim 11, wherein the surgical table is generally rectangular, and wherein the gap includes a recess in the rectangular surgical table.

13. The surgical table of claim 11, wherein the gap is configured to fit a front profile of a robotic arm of the surgical robot.

14. The surgical table of claim 11, wherein the first leg support includes an articulation portion, the articulation portion configured to be adjusted up or down relative to the first leg support, wherein the articulation portion is configured to lift a femur of the first leg of the patient to perform a soft tissue pull test.

15. The surgical table of claim 11, wherein the first leg support includes an articulation portion, the articulation portion configured to be adjusted up or down relative to the first leg support, wherein the articulation portion is actuatable by a robotic arm of the surgical robot, and wherein the articulation portion includes a force sensor to determine an amount of force on a portion of the first leg of the patient.

16. The surgical table of claim 11, wherein the knee-activated actuator is located at a position at least 12 inches above a portion of the surgical table that is configured to be in contact with a floor.

17. The surgical table of claim 11, wherein the first leg support further includes a pneumatic cuff to support the first leg, wherein the pneumatic cuff is inflated via a pneumatic line operably coupled to the pneumatic cuff from a robotic arm support of the surgical robot.

18. The surgical table of claim 11, wherein the first leg support extends along a first longitudinal axis, and wherein the second leg support extends along a second longitudinal axis, and wherein the first and second longitudinal axis are between 0 and 45 degrees apart.

19. The surgical table of claim 11, wherein the gap is formed as a recess and has a recess width from the first leg support to the second leg support, and a maximum recess width is between 6-24 inches.

20. The support system of claim 1, further comprising the robotic arm coupled to the robotic arm support.

* * * * *

UNITED STATES PATENT AND TRADEMARK OFFICE
CERTIFICATE OF CORRECTION

PATENT NO. : 11,039,892 B2
APPLICATION NO. : 16/225648
DATED : June 22, 2021
INVENTOR(S) : Harlan Levine Page 1 of 1

It is certified that error appears in the above-identified patent and that said Letters Patent is hereby corrected as shown below:

In the Claims

In Column 17, Line 37, in Claim 7, before "wherein", delete "and"

Signed and Sealed this
Nineteenth Day of October, 2021

Drew Hirshfeld
*Performing the Functions and Duties of the
Under Secretary of Commerce for Intellectual Property and
Director of the United States Patent and Trademark Office*